United States Patent [19]

Thies et al.

[11] Patent Number: 4,891,384

[45] Date of Patent: Jan. 2, 1990

[54] VALEPOTRIATE HYDRIN CONTAINING MEDICINES USED TO TREAT UCLERS AND MOTILITY DISTURBANCES

[75] Inventors: Peter W. Thies; Samuel David; Insa Hell, all of Hannover; Klaus-Ulrich U. Wolf, Haenigsen, all of Fed. Rep. of Germany

[73] Assignee: Kali-Chemie Pharma GmbH, Hannover, Fed. Rep. of Germany

[21] Appl. No.: 191,819

[22] Filed: May 3, 1988

Related U.S. Application Data

[60] Division of Ser. No. 68,715, Jun. 30, 1987, abandoned, which is a continuation of Ser. No. 636,414, Jul. 31, 1984, abandoned.

[30] Foreign Application Priority Data

Aug. 2, 1983 [DE]  Fed. Rep. of Germany ....... 3327811

[51] Int. Cl.$^4$ .............................................. A61K 31/35
[52] U.S. Cl. .................................... 514/456; 549/396; 514/927; 514/926
[58] Field of Search ....................... 514/456, 927, 926; 549/396

[56] References Cited

U.S. PATENT DOCUMENTS

| | | | |
|---|---|---|---|
| 3,422,090 | 1/1969 | Thies et al. | 260/236.5 |
| 3,812,154 | 5/1974 | Thies | 260/340.3 |
| 3,917,651 | 11/1975 | Thies | 260/340.3 |
| 4,189,323 | 2/1980 | Buhr | 430/281 |
| 4,239,850 | 12/1980 | Kita et al. | 430/281 |
| 4,313,930 | 2/1982 | Wischniewski et al. | 424/32 |
| 4,391,819 | 7/1983 | Thies et al. | 424/278 |

FOREIGN PATENT DOCUMENTS

| | | |
|---|---|---|
| 2654709 | 6/1978 | Fed. Rep. of Germany . |
| 2230626 | 7/1978 | Fed. Rep. of Germany . |
| 3112737 | 10/1982 | Fed. Rep. of Germany . |
| 1388492 | 3/1975 | United Kingdom . |

OTHER PUBLICATIONS

Patent Abstracts of Japan, Vol. 5, Number 89 (C-58) [761], June 10, 1981, Japanese Patent Application No. 56-34627.

Patent Abstracts of Japan, Vol. 5, No. 160 (C-75) [832], October 15, 1981, Japanese Patent Appl. No. 56-90011.

Tetrahedron Letters No. 15, (1976) J. Hoelzl et al., "Zur Struktur Von Drei Genuinen Valtrathydrinen Aus Valeriana Tiliaefolia", pp. 1171–1174.

Comptes rendus de l'Academie Bulgare des Sciences, No. 5, 1975, S.S. Popov et al., "Biogenetic Relationship Between Some Valepotriates", pp. 651–653.

Tetrahedron Vol. 29, No. 15, 1973, P.W. Thies, "Ueber Die Wirkstoffe Des Baldrians-X$^1$", pp. 3213–3226.

Tetrahedron Vol. 24, 1968, P.O. Thies, "Die Konstitution Der Valepotriate", pp. 313–347.

P. W. Thies et al., "Assignment of Type and Location of the Acyloxy Substituents in Valepotriates via C13-NMR-Spectroscopy", Planta Medica Journal of Medicinal Plant Research, No. 1, 1981, Vol. 41, pp. 15–20.

*Primary Examiner*—Nicky Chan
*Attorney, Agent, or Firm*—Foley & Lardner, Schwartz, Jeffery, Scfhwaab, Mack, Blumenthal & Evana

[57] ABSTRACT

The use of valepotriate hydrins in the prevention and treatment of disorders of the gastrointestinal tract is described, together with pharmaceutical compositions containing valepotriate hydrins and certain novel valepotriate hydrins per se.

15 Claims, No Drawings

VALEPOTRIATE HYDRIN CONTAINING MEDICINES USED TO TREAT UCLERS AND MOTILITY DISTURBANCES

This application is a division of application Ser. No. 068,715, filed June 30, 1987, which is a continuation of Ser. No. 636,414, filed July 31, 1984, both abandoned.

BACKGROUND OF THE INVENTION

The present invention relates to the use of valepotriatehydrins for the prevention and treatment of peptic ulcers and for the treatment of cramp-like disturbances in the gastrointestinal tract of mammals, including humans, and to novel valepotriate hydrins with peptic ulcer formation-inhibiting and motility-normalizing properties.

Valepotriates are compounds of Formula II

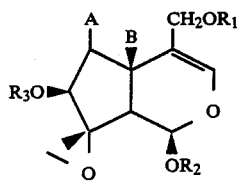

wherein A denotes hydrogen, B denotes hydrogen or hydroxy, or A and B together denote a bond; and of the substituents $R_1$, $R_2$ and $R_3$, one denotes an isovaleroyl group, another denotes an acetyl group, and the other denotes an acyl group of one of the following acids: isovalerianic acid, $\beta$-methylvalerianic acid, $\alpha$-isovaleroyloxyisovalerianic acid, $\alpha$-acetoxyisovalerianic acid, $\beta$-acetoxyisovalerianic acid, $\beta$-acetoxy-$\beta$-methylvalerianic acid, or $\beta$-hydroxyisovalerianic acid. Valepotriates are known as the pharmacologically active ingredients of valerian and other plants of the family of the valerianeae See, for example, Thies, *Tetrahedron* 24: 313-317 (1968) and Thies et al, *Planta Medica* 41: 15-20 (1981). The known valepotriates include valtratum (A+B=a bond, $R_1$=acetyl, $R_2$=isovaleroyl, $R_3$=isovaleroyl), isovaltratum (A+B=a bond, $R_1$=isovaleroyl, $R_2$=isovaleroyl, $R_3$=acetyl), acevaltratum (A+B=bond, $R_1$=acetyl, $R_2$=isovaleroyl, $R_3$=acetoxyisovaleroyl), and didrovaltratum (A+B=a hydrogen atom each, $R_1$=isovaleroyl, $R_2$=isovaleroyl, $R_3$=acetyl). With the valepotriates, in valepotriate mixtures obtained from plants, analogous homocompounds are frequently present in which an isovaleroyl group of the corresponding valepotriate is replaced by $\beta$-methylvaleroyl. Valepotriates are known for their effects on the central nervous system, especially calming and psychic stabilization, and also spasmolytic activity. These effects of valerian and its active ingredients have been used pharmaceutically for a long period of time.

In the course of work to elucidate the structure and to prepare chemical derivatives of valepotriates, certain halide and rhodano hydrins of the four valepotriates mentioned above have been prepared and described. Thus, for example, the iodohydrins, rhodanohydrins and bromohydrins of valtratum, acevaltratum and didrovaltratum (*Tetrahedron* 24: 313-317 and German Offenlegunsschrift Nos. 19 61 433 and 30 26 579), the chlorohydrin of valtratum (*C.R. acad. Bulg.* 28: 651 (1979)), and the iodohydrin and rhodanohydrin of isovaltratum (*Tetrahedron* 19: 3213-3226 (1973)) are known as intermediate products. The acetohydrin of didrovaltratum is also known as an intermediate product. Furthermore, certain hydrins of the best known valepotriates have been described wherein X signifies an acid group of an acid naturally occurring in valerian plants, particularly the isovaleroylhydrin of valtratum, acevaltratum, isovaltratum and didrovaltratum, together with the acetohydrins of valtratum and isovaltratum. See *Tetrahedron Letters:* 1171 (1976). No pharmacological properties have been disclosed heretofore for these valepotriate hydrins which have been prepared as intermediate products or which have otherwise been specifically described.

In German Offenlegunsschrift No. 31 12 732, a process for obtaining a valerian extract free of epoxy which possesses sedating-active ingredients, and which allegedly contains valepotriate hydrins, among others, is described. But no individual valepotriate hydrins or their effects are described more specifically.

SUMMARY OF THE INVENTION

It is therefore an object of the present invention to provide novel pharmaceutical preparations for the treatment and prevention of diseases of the gastrointestinal tract.

It is a further object of the present invention to provide novel valepotriate hydrins which possess valuable pharmacological properties.

It is another object of the present invention to provide a process for synthesizing various novel valepotriate hydrins.

In accomplishing the foregoing objects, there has been provided, in accordance with one aspect of the present invention, a pharmaceutical composition for treating the gastrointestinal tract of a mammal, comprising a physiologically compatible carrier and a gastrointestinal tract-normalizing amount of an active ingredient comprising a compound having Formula I:

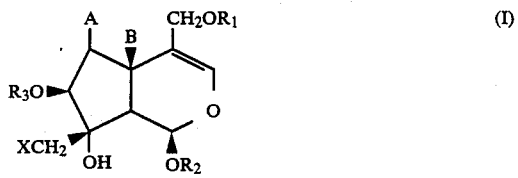

wherein
A denotes a hydrogen
B denotes a hydrogen or a hydroxy: or
A and B together denote a bond: of $R_1$, $R_2$ and $R_3$,
(i) one denotes an isovaleroyl group,
(ii) another an acetyl group, and
(iii) the other denotes an acyl group of an acid selected from the group consisting of isovalerianic acid, $\beta$-methylvalerianic acid, $\overline{a}$-isovaleroyloxyisovalerianic acid, $\overline{a}$-acetoxyisovalerianic acid, $\beta$-acetoxyvalerianic acid, $\beta$-acetoxy-$\beta$-methylvalerianic acid, and $\beta$-hydroxyisovalerianic acid; and X denotes a halogen, a cyano, a rhodano, an azido, or an acyloxy group having the formula $R_4COO$ wherein $R_4$ denotes
(a) an unsubstituted or hydroxy-substituted alkyl group comprising 1 to 20 carbon atoms, (b) an alkenyl group comprising 3 to 20 carbon atoms, or (c) a constituent selected from the group consisting of a phenyl, a phenylalkyl comprising an alkylene chain containing up to 3 carbon atoms, and a phenylalkenyl group comprising an alkenylene chain containing up to 3 carbon atoms, said constituent be unsubstituted or substituted on the phenyl ring by a halogen, a trifluoromethyl, a hydroxy, lower alkyl, or a lower alkoxy.

In accordance with another aspect of the present invention, there has been provided a compound of the Formula Ia

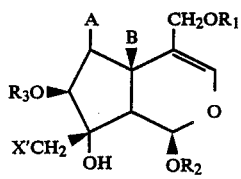

(Ia)

wherein
A denotes a hydrogen
B denotes a hydrogen or a hydroxy, or
A and B together denote a bond; of $R_1$, $R_2$ and $R_3$,
(i) one denotes an isovaleroyl group,
(ii) another an acetyl group, and
(iii) the other denotes an acyl group of an acid selected from the group consisting of isovalerianic acid, β-methylvalerianic acid, α-isovaleroyloxyisovalerianic acid, α-acetoxyisovalerianic acid, β-acetoxyisovalerianic acid, β-acetoxy-β-methylvalerianic acid, and β-hydroxyisovalerianic acid; and X' denotes a cyano, an azido, or an acyloxy group having the formula $R_4COO$ wherein $R_4$ denotes (a) a constituent selected from the group consisting of ethyl, propyl, isopropyl, n-butyl, 1-methylpropyl, and tert-butyl, said constituent being unsubstituted or hydroxy-substituted, (b) a constituent selected from the group consisting of an alkyl comprising 5 to 20 carbons and an alkenyl comprising 3 to 20 carbons, said constituent being unsubstituted or hydroxy-substituted, (c) a constituent selected from the group consisting of a phenyl, a phenylalkyl, or a phenylalkenyl comprising an alkylene or alkenyl chain containing up to 3 carbon atoms, said constituent being unsubstituted or substituted on the phenyl ring with a halogen, a trifluoromethyl, a hydroxy, a lower alkyl, or a lower alkoxy or, if B denotes hydroxy and/or $R_2$ is not isovaleroyl, and/or one of $R_1$ and $R_3$ is acetyl and the other is not isovaleroyl X' denotes halogen, acetoxy, or rhodano;
A and B together denote a bond,
X' denotes chlorine,
$R_1$ and $R_2$ each separately denote isovaleroyl, and
$R_3$ denotes acetyl, or
$R_1$ denotes acetyl,
$R_2$ denotes isovaleroyl, and
$R_3$ denotes acetoxyisovaleroyl.

Also provided is a process for synthesizing the valepotriate compounds mentioned in the preceding paragraph, comprising the step of reacting (1) a compound of Formula II

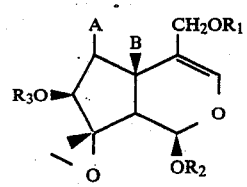

(II)

wherein A, B, $R_1$, $R_2$, and $R_3$ each is as defined above, with (2) an alkali metal salt or a quaternary ammonium salt of an acid compound having the formula (III)

$$H-X \qquad (III)$$

wherein X' is as defined above, in a solvent which is inert during said reacting.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has now been discovered that valepotriate hydrins of Formula I surprisingly possess valuable pharmacological properties, including, in particular, a favorable pharmacological effect on the gastrointestinal tract. They are characterized by a protective action on the gastrointestinal mucosa, and by an inhibiting effect on the formation of peptic ulcers and good effectiveness against cramp-like motility disorders, with good tolerance and low toxicity.

In view of their effect in the gastrointestinal tract of mammals, including humans, the valepotriate hydrins of Formula I are suitable for use as medicines in gastroenterology.

As the active ingredients according to the invention, individual valepotriate hydrins or valepotriate hydrin mixtures may be used, for example, hydrin mixtures prepared from valepotriate mixtures obtained from extracts of roots and rhizoma of different species of Valerianeae and Kenthranteae. Valepotriate hydrins of Formula I are suitable wherein $R_1$ is isovaleroyl or α-isovaleroyloxyisovaleroyl and $R_3$ is acetyl, or wherein $R_1$ is acetyl and $R_3$ isovaleroyl or β-acetoxyisovaleroyl, and $R_2$ signifies isovaleroyl or β-methylvaleroyl.

Among the valepotriate hydrins with a diene structure (A+B=bond), the hydrins of valtratum, isovaltratum, homovaltratum, homoisovaltratum, acevaltratum and homoacevaltratum, or their mixtures, are considered suitable. Chlorohydrin, acetohydrin, and isovaleroyloxyhydrin are especially suitable.

Among the valepotriate hydrins with a monoene structure (A and B are each a hydrogen atom), the hydrins of didrovaltratum, homodidrovaltratum, or their mixtures can be utilized. For example, didrovaltrathalogen hydrins, preferably didrovaltratechlorohydrin, didrovaltratalkanoyloxyhydrins, preferably didrovaltratisovaleroyloxyhydrin or didrovaltratacetoxyhydrin; aromatic didrovaltratacyloxyhydrins, preferably benzoyloxyhydrins or phenacetyloxyhydrins, either of which is optionally substituted with chlorine on the phenyl ring; as well as mixtures of these didrovaltrathydrins with the corresponding homodidrovaltrathydrins, can be employed in the present invention.

Among the valepotriate hydrins, wherein A is hydrogen and B is hydroxy, the hydrins of isovaleroyloxyhydroxydidrovaltratum (IVHD) for example, IVHD-chlorohydrin, are considered suitable.

In the valepotriate hydrins used according to the present invention, when X represents a halogen it is appropriately chlorine, bromine, or iodine, particularly, chlorine. Similarly to the valepotriate hydrins in which X is a halogen, valepotriate hydrins in which X is rhodano, cyano or azido, are also suitable.

If X represents an aliphatic carboxylic acid group in the valepotriate hydrins used according to the present invention, the alkyl or alkenyl groups $R_4$ contained therein may be straight or branched, and may contain up to 20, preferably up to 10, and in particular up to 6, carbon atoms. The following are cited as examples of suitable aliphatic carboxylic acid groups X: acetoxy, propionyloxy isopropionyloxy, n-butyryloxy, sec-butyryloxy, n-valeroyloxy, isovaleroyloxy, 2-hydroxypropionyloxy, caprinoyloxy, lauroyloxy, stearyloxy, propargyloxy, oleyloxy, and cinnamoyloxy.

If X represents an aromatic carboxylic acid group, the phenyl group contained in the group $R_4$ may be unsubstituted or may be substituted with 1 to 3 substituents selected from the group of lower alkyl, lower alkoxy, hydroxy, trifluoromethyl and halogen. Among these substituents, the halogens, lower alkoxy and lower alkyls are especially suitable. Lower alkyl or alkoxy groups may contain 1 to 3 carbon atoms and may be, in particular, methyl or methoxy. The preferred halogen is chlorine.

The compounds of Formula I have novel, valuable pharmacological effects in the gastrointestinal tract. In particular, the compounds unexpectedly possess the ability o stabilize the gastrointestinal mucosa against different harmful effects and to inhibit the formation of peptic ulcers.

The compounds of Formula I further have the ability to counteract motility disorders in the gastrointestinal tract, in particular cramp-like disorders of spontaneous motility in the intestines, and to inhibit the mechanical hyperactivity of the colon.

The pharmacological properties of the valepotriate hydrins, used therapeutically according to the present invention in gastroenterology, have been demonstrated in standard laboratory animals, using well-recognized pharmacological tests, as is apparent from the following data.

1. Determination of acute toxicity

The acute 7 day toxicity was determined after a single oral application in white NMRI mice which had been previously fasted. The $LD_{50}$ value, defined as the dose corresponding to a 50% mortality of the animals on the seventh day following the application, was not attained in any of the substances investigated in doses up to 2150 mg/kg.

2. Determination of the inhibiting effect against aspirin induced erosion and ulcer formation.

It is known that nonsteroidal antiphlogistic drugs have a harmful effect on mucosa linings. According to the present invention, this adverse side effect can be substantially avoided with valepotriate hydrins, reflecting a therapeutically protective, positive effect on the mucosa.

Test method:

Groups of at least 6 male rats with a body weight of 180 to 200 g per test dose were used. The test substances were administered orally in 0.5 ml of the suspension medium (2% tylose solution) per 100 g of the weight of the animal. A control group of animals received only the corresponding volume of the suspension medium. One hour following the application of the test substances, the animals were given oral 200 mg/kg acetylsalicylic acid per 100 g of animal weight, again suspended in 0.5 ml of the suspension medium, to produce ulcers. The animals were killed five hours after the application of the irritant. The number and size of the ulcers formed were evaluated. The evaluation was carried out in manner adapted from O. Munchow, *Arzneim. Forsch.* 4: 341–344 (1954).

Mean values (ulcer index) and standard deviations were calculated and the inhibiting effect of the test substances determined in percentage with respect to the control group.

3. Determination of the inhibiting effect on the spontaneous activity of the colon in anesthesized rats.

Test method:

Male rats with body weights of 200–350 g were anesthesized by the intraperitoneal (i.p.) application of 10 mg xylazine and 50 mg ketamine/kg as a bolus and thereafter by the continuous i.p. infusion of the same dose/h.

The rectum and the colon were then emptied. The animals were tracheotomized and laparotomized, and were kept on a hot plate to maintain their body temperature. A button cannula, equipped at its tip with a synthetic plastic balloon (10 ml diameter), was introduced rectally and placed in the colon. After having been filled with 3 ml water, the balloon catheter was connected with a Statham pressure transducer. Pressure variations in the colon were continuously recorded by means of a multirecorder. Pressure amplitudes of the colon, in ml of water, and the frequency of pressure variations were measured. To determine their effect, the test substances were dissolved in a physiological sodium chloride solution or suspended in tylose and administered i.p. or intraduodenally. The averaged colon pressure values before and after the application of the test substances were compared and evaluated with the aid of the Student t-test.

In the above-mentioned test methods the compounds of Formula I generally exhibited satisfactory results with a dosage range of 20–250 μmole/kg. Table 1 summarizes the results obtained. The numbers assigned to the test substances relate to the numbers of the examples presented below to illustrate the present invention.

| Example No. | Inhibiting action on aspirin induced stomach ulcer formation in rats | | Effect on spontaneous motility of the colon in rats | | |
|---|---|---|---|---|---|
| | Dose in μMol/kg p.o. | % Inhibiting action | Dose in μMol/kg | Change in pressure amplitude | % Frequency variation |
| 2 | 46.4 | 75 | 46.4 i.d. | −33 | |
| 3 | 46.4 | 65 | 100 i.p. | −48 | |
| 3a | 46.4 | 77 | 100 i.p. | −14 | −19 |
| 5 | 46.4 | 50 | | | |
| 9 | 46.4 | 56 | 100 i.p. | −81 | −25 |
| 10 | 46.4 | 77 | 100 i.p. | −14 | −54 |
| 13 | 46.4 | 76 | 100 i.p. | −42 | −31 |
| 14 | 46.4 | 59 | 100 i.p. | −24 | −55 |
| 15 | 100. | 57 | 100 i.p. | +14 | −4 |
| 16 | 46.4 | 45 | 100 i.p. | +4 | −14 |
| 17 | 100. | 59 | 100 i.p. | −72 | −73 |
| 18 | 46.4 | 52 | | | |
| 19 | 100. | 60 | 100 i.p. | −28 | −36 |
| 20 | 46.4 | 64 | 100 i.p. | −28 | −55 |
| 21 | 46.4 | 77 | — | — | — |
| 22 | 100. | 23 | 100 i.p. | −58 | 0 |
| 1 | 21.5 | 64 | 100 i.d. | 0 | −31 |
| 24 | 100. | 53 | — | — | — |

Based on their effects on the gastrointestinal tract, the valepotriate hydrins of Formula I are suitable in gastroenterology as drugs for the prevention and treatment of cramp-like motility disorders or colon irritable in mammals, including humans.

The doses to be applied may differ from individual to individual, and may vary depending on the nature of the condition to be treated, the substance employed, and the nature of the drug's application. For example, parenteral formulations in general contain less of the active ingredient than oral preparations. But generally, for administration to humans and large mammals, pharmaceutical compositions with an active ingredient content of 20–250, in particular 25–75 μmole per single dose are suitable.

The present invention further relates to novel valepotriate hydrins of Formula I, particularly polyacyloxycyclopenta(c)pyran compounds of Formula Ia

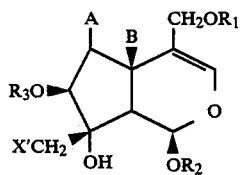 (Ia)

wherein
(1) A is hydrogen and B hydrogen or hydroxy, or A and B together denote a bond; of $R_1$, $R_2$ and $R_3$, one denotes an isovaleroyl group, another an acetyl group, and the other denotes an acyl group of an acid selected from one of the following acids: isovalerianic acid, β-methylvalerianic acid, α-isovaleroyloxyisovalerianic acid, α-acetoxyisovalerianic acid, β-acetoxyisovalerianic acid, β-acetoxy-β-methylvalerianic acid or β-hydroxyisovalerianic acid, and X' stands for cyano, azido or an acyloxy group $R_4COO$, wherein $R_4$ is ethyl, propyl, isopropyl, n-butyl, 1-methylpropyl or tert-butyl optionally substituted with hydroxy, an alkyl group with 5 to 20 carbon atoms optionally substituted with hydroxy, an alkenyl group with 3–20 carbon atoms, or a phenyl, phenylalkyl or phenylalkenyl group with up to 3 carbon atoms in the alkylene or alkenylene chain which may be substituted in the phenyl ring by halogen, trifluoromethyl, hydroxy, a lower alkyl or a lower alkoxy, or (2) If B is hydroxy and/or $R_2$ is not isovaleroyl and/or if one of the groups $R_1$ and $R_3$ is acetyl and the other is not isovaleroyl, X' can also signify halogen, acetoxy, or rhodano, or (3) A and B together form a bond, X' represents chlorine, $R_1$ and $R_2$ each are isovaleroyl and $R_3$ is acetyl, or $R_1$ is acetyl, $R_2$ is isovaleroyl and $R_3$ is β-acetoxyisovaleroyl.

The present invention also relates to the preparation of the aforementioned, novel valepotriate hydrins.

Valepotriate hydrins of Formula I may be prepared from the corresponding valepotriates of Formula II, by opening the epoxy ring of the latter compounds by the addition of acid.

For this purpose, the valepotriates of Formula II are reacted with an alkali metal salt or a quaternary ammonium salt of an acid of Formula III $$H-X \qquad (III)$$

wherein X has the above-mentioned significance, in a solvent inert under the conditions of the reaction.

Sodium and potassium salts are especially suitable as the alkali metal salts of the acids of Formula III. Trialkylammonium or tetraalkylammonium; or benzyldialkylammonium or benzyltrialkylammonium salts wherein the alkyl groups are lower alkyl groups preferably containing 1 to 4 carbon atoms; or salts of cyclic amines, for example, pyridinium, pyrrolidinium and N-lower alkyl pyrrolidinium salts, are appropriate as the quaternary ammonium salts. As examples of suitable quaternary ammonium salts, the following are cited: tetrabutylammonium, triethylammonium, tetramethylammonium, benzyltriethylammonium, and pyridinium salts. Quaternary ammonium salts of the acids of Formula III may be formed, if desired, in situ from the corresponding amines.

Suitable inert solvents are, for example, halogenated hydrocarbons, such as methylene chloride and chloroform; aromatic hydrocarbons, such as benzene and toluene; acetonitrile; glacial acetic acid; and lower alcohols or mixtures of said solvents. If alkali metal salts are used, the reaction solution may also comprise a mixture of the aforementioned solvents with water, for example, lower alcohols/water and glacial acetic acid/water. If water-containing solvents and/or alkali metal salts of the acids of Formula III are used, it may be advantageous, for the purpose of buffering the reaction mixture to a pH range of 3 to 7, to add buffer salts, for example, sodium acetate or ammonium chloride. Conveniently, for the buffering of the base liberated in the course of the reaction, adequate amounts of the acid inert under the conditions of the reaction or of an acid of Formula III may be added. If the acid of Formula III is an organic carboxylic acid, the excess of this acid may serve as the solvent. The reaction may be conducted, for example, so that the valepotriate is dissolved in the acid and a quaternary ammonium salt of the acid is formed in situ by the addition of a quaternary amine.

It has been found to be appropriate, especially when alkali metal salts of the acids of Formula III are used, to add an inorganic tetraalkylammonium salt or a tetraalkylphosphonium salt suitable as a phase transfer catalyst, for example, a halide or a hydrogen sulfate. Lower alkyl ammonium salts, wherein the alkyl groups contain for example 2 to 4 carbon atoms, are used preferably as the tetraalkylammonium salts. In the tetraalkylphosphonium salts, alkyl groups with 1 to 20 carbon atoms may be incorporated. Tetrabutylammoniumhydrogen sulfate, tetrabutylammonium chloride, and hexadecyltributylphosphonium bromide are cited as examples of salts suitable as catalysts.

The reaction temperature may be between 0° and 120° C., depending on the reactivity of the acid group to be introduced, and the reaction time may vary between about one-half hour and about 24 hours.

The valepotriate hydrins of Formula I or their mixtures may be isolated in a known manner from the reaction mixture.

Generally, as the initial substances of Formula II, valepotriate mixtures obtained from natural plant extracts are used, which in addition to the principal valepotriate also contain subordinate quantities of isomeric or closely related valepotriates which occur in the plant. Thus, the valepotriates of Formula II used in accordance with the claimed invention often contain admixtures of the corresponding homocompounds of Formula II, wherein an isovaleroyloxy group is replaced by a methylvaleroyloxy group. The ratio of the principal component to the corresponding homocompound present in the starting material of Formula II is preserved in the conversion and also occurs in the final product of Formula I. The ratio of the principal component to the corresponding homocompound and the other isomers potentially present can be determined in the initial product and/or end product in a known manner using $^{13}$C-NMR spectroscopy.

If desired, pure isomer compounds may be separated from existing mixtures, both at the stage of forming the initial valepotriates of Formula II and at the stage of forming the valepotriates of Formula I, by column chromatography, preferably high pressure liquid column chromatography.

The compounds of Formula I may be combined, according to the present invention, together with conventional pharmaceutical auxiliary and/or carrier substances in solid or liquid pharmaceutical preparations. Examples of solid preparations include orally administrable forms, such as capsules, tablets, granules or dragees, and suppositories. Solid preparations may contain pharmaceutically customary inorganic and/or organic carrier substances, such as talcum, lactose and starch, in addition to conventional pharmaceutical auxiliary substances, for example lubricants, such as magnesium stearate, or tablet-disintegrating agents. Liquid preparations, such as solutions, suspensions or emulsions, may contain the usual diluting substances, such as water, oils, e.g., triglyceride mixtures of saturated vegetable fatty acids and vaseline, and/or suspending agents, such as polyethylene glycols. Further auxiliary substances may be added, such as preservatives, stabilizers, flavoring agents, and the like.

If desired, solid oral forms of the drugs may contain substances delaying the release of the active ingredient, such as polyvinyl acetate, acrylatecopolymers and methacrylatecopolymers, higher fatty alcohols, and other wax-like substances.

The active ingredients may be mixed and formulated with the pharmaceutical auxiliary and/or carrier substances in a known manner. If desired, the active ingredients may initially be microencapsulated, for example, by the method described in German Offenlegungsschrift No. 28 49 029. To produce solid compositions, the active ingredients, optionally in the microencapsulated form, may be mixed and granulated together with the auxiliary and/or carrier substances, in the usual manner, by a wet or dry process. Depending on the type of the auxiliary substances used, in some cases a directly pelletable powder may be obtained.

The granules or powder may be filled directly in capsules or pressed in a conventional manner into tablet cores. If desired, the latter may be coated in a known fashion. Also if desired, the tablets, dragees and capsules may be provided in a known manner with a gastric juice-resistant coating.

If so desired, the valepotriate hydrins may be placed in soft gelatin capsules suspended or dissolved in a liquid carrier substance.

The examples below further describe the invention without restricting its scope in any way.

EXAMPLE 1

Isovaltratchlorohydrin 25 g of isovaltratum (containing approximately 10% valtratum) were dissolved in 100 ml of methylene chloride, and the solution was reacted with 40 g of tetrabutylammonium chloride. The reaction mixture was heated for approximately 6 hours at 60° C.

Subsequently, the mixture was diluted with water for working up and extracting with ether. The organic phase was washed once with water, dried over sodium sulfate, filtered, and evaporated to dryness in vacuum. The raw product remaining as the residue (about 30 g) was purified by means of column chromatography over aluminum oxide using 5–10% 2-butanone containing n-hexane as the eluting agent. 22.97 g of the purified product were obtained, which product also contained valtratchlorohydrin, in addition to isovaltratchlorohydrin. After repeated recrystallization from n-hexane/ether, 7.8 g of pure isovaltrachlorohydrin were obtained.

M.P.: 78°–79° C. $[a]_D^2 = +187.5°$ (c=1 in $CH_2Cl_2$)

EXAMPLE 2

Didrovaltratisovaleroyloxyhydrin 60 g of didrovaltratum (containing approximately 20% homodidrovaltratum) were dissolved in 135 ml of isovalerianic acid and the solution reacted with 24 ml of triethylamine and 21 g of tetrabutylammoniumhydrogen sulfate. The reaction mixture is heated for 14 hours at 60° C. Subsequently, for processing, the reaction mixture was poured carefully into ice water, and the mixture gently neutralized with a solution of sodium bicarbonate and extracted with ether. The organic phase was dried over sodium sulfate, filtered, and evaporated in vacuum to dryness. The remaining raw product was purified chromatographically over 250 g of silica gel, using n-hexane/ether as the eluting agent. 91 g of the raw product, still containing isovalerianic acid, were obtained. The purification was repeated over silica gel. 65.81 g of the purified product were obtained. The latter was taken up in ether and extracted once with water, once with a sodium bicarbonate solution, and again with water. Subsequently, the ether phase was dried over sodium sulfate, clarified with charcoal, filtered and evaporated under reduced pressure to dryness. 54.46 g of oily didrovaltratisovaleroyloxyhydrin (containing approximately 20% homodidrovaltratisovaleoyloxyhydrin) were obtained.

$[a]_D^{20} = -19°$ (c=1 in CH$_3$OH)

EXAMPLE 3

Didrovaltratchlorohydrin (homodidrovaltratchlorohydrin-containing)

26 g of didrovaltratum (containing approximately 20% homodidrovaltratum) were dissolved in 100 ml of acetonitrile and the solution was reacted with 56 g of benzyltriethylammonium chloride and 13 ml of glacial acetic acid and heated for approximately 4 hours at 60° C. Subsequently, the reaction mixture was cooled for processing, diluted with water, and extracted with ether. The ether phase was washed three times with water, dried over sodium sulfate, filtered, and evaporated in vacuum to dryness. The brown raw product remaining as the residue was purified over silica gel, using up to 20% 2-butane containing n-hexane as the eluting agent. The eluate was evaporated to dryness, the residue was taken up in ether, and the resulting solution was washed with a sodium bicarbonate solution and then washed again three times with water. The residue was thereafter dried over sodium sulfate, clarified with charcoal, filtered, and evaporated in vacuum to dryness.

20.6 g of an oily didrovaltratchlorohydrin (containing about 20% homodidrovaltratchlorohydrin) were obtained.

$[a]_D^{20} = -16.8°$ (c=1 in CH$_3$OH)

EXAMPLE 3a

Didrovaltratchlorohydrin (pure)

(A) Preparation of the pure didrovaltratum initial product 500 g of aluminum oxide were slurried in 2450 ml of petrolether and 50 ml of glacial acetic acid, and were then placed in a column and washed free of acid with n-heptane. 5 g of raw didrovaltratum (containing approximately 15% homodidrovaltratum and 5% isovaltratun) were charged into the column and eluted with n-heptane in fractions.

The fractions containing only didrovaltratum were evaporated in vacuum and the didrovaltratum remaining as the residue was recrystallized from ether/n-hexane.

Mp: 63°-64° C.; yield 1.6 g.

From the fractions largely free of didrovaltratum, raw homodidrovaltratum (containing about 10% isovaltratum) was obtained as the residue by evaporation.

(B) Preparation of didrovaltratchlorohydrin.

0.82 g of didrovaltratum was dissolved in 20 ml of methylene chloride, and the solution was reacted with 0.9 g of benzyltriethylammonium chloride and 0.4 g of maleic acid. The reaction mixture was agitated for 24 hours at room temperature. It was then extracted twice with water, and the organic phase was dried over sodium sulfate, filtered, and evaporated in vacuum. The remaining residue was purified over silica gel using n-hexane/2-butanone as the eluting agent. 0.82 g (corresponding to a yield of 92%)of pure didrovaltratchlorohydrin was obtained as an oil.

$[a]_D^{20} = -20.60°$ (c=1 in CH$_3$OH).

EXAMPLE 3b

Homodidrovaltratchlorohydrin (pure)

0.8 g raw homodidrovaltratum (containing approximately 10% isovaltratum, prepared according to Example 3a (A), was converted by the method of Example 3a (B) into the corresponding chlorohydrin. Pure homodidrovaltratchlorohydrin was isolated from the raw product by high pressure liquid chromatography (HPLC) using silica gel with a grain size of 0.007 ml (commercial product Lichrosorp of the Merck Co.) with 99.5:0.5 n-hexane/ethanol as the eluting agent.

$[a]_D^{20} = -20.60°$ (c=1 in CH$_3$OH)

EXAMPLE 4

Didrovaltratazidohydrin 2.12 g didrovaltratum (containing approximately 20% homodidrovaltratum) were dissolved in 50 ml of methanol and 10 ml of water, and the solution was then reacted with 6.65 g of sodium azide and 5.53 g of ammonium chloride. The reaction mixture was allowed to stand at room temperature for approximately 12 hours. Subsequently, the mixture was diluted with ice water for processing and was extracted with ether. The ether phase was dried over sodium sulfate, clarified on charcoal, filtered, and evaporated in vacuum to dryness. 1.66 g of oily didrovaltratazidohydrin (containing about 20% homodidrovaltratazidohydrin) were obtained (corresponding to a yield of 71%).

$[a]_D^{20} = -38.6°$ (c=1 in CH$_3$OH)

EXAMPLE 5

Didrovaltratacetohydrin 10 g of didrovaltratum (containing about 20% homodidrovaltratum) were dissolved in 11 ml of glacial acetic acid and 1.1 ml of acetic acid anhydride at 80° C. The solution was cooled to 20° C. and reacted with 25 ml of triethylamine. The solution was subsequently heated to 80° C. for 2.5 h. The solution was then poured into ice water for processing and extracted with ether. The ether extracts were dried over sodium sulfate, filtered and evaporated in vacuum. 9.9 g of didrovaltratactoxyhydrin (containing about 20% homodidrovaltratacetoxyhydrin) were obtained (corresponding to a yield of 85.9%).

$[a]_D^{20} = -38.0°$ (c=1 in CH$_3$OH)

EXAMPLE 6

Valtratrhodanohydrin 6.0 g of valtratum and 12 g of sodium acetate were dissolved in 60 ml of glacial acetic acid and reacted with a solution of 2.775 g of potassium rhodanide in 14 ml of water. The reaction mixture was allowed to stand for 12 hours at a temperature between 0° and 5° C. Subsequently, the mixture was diluted for processing with twice the amount of water and extracted four times with 50 ml of ether each time. The combined ether phases were washed with water, dried over magnesium sulfate with the addition of charcoal, filtered, and evaporated in vacuum. A colorless oil was obtained which crystallized very rapidly. After recrystallization from ether/benzene, valtratrrhodanohydrin was obtained with a yield of 75%.

Mp: 106°–109° C. $[a]_D^{20} = +209.17°$ (c=1 in $CH_3OH$)

EXAMPLE 7

Valtratbromohydrin 2.5 g of valtratum and 2 g sodium acetate were dissolved in 10 ml of glacial acetic acid and reacted with a solution of 0.25 g of sodium bromide in 2 ml of water. The mixture was allowed to stand for 2 days at 22° C. It was then diluted for processing with water and extracted with ether/benzene, and the organic phase was then washed free of acid with water, dried over magnesium sulfate with charcoal added, filtered, and vaporated. The initially oily residue crystallized after rubbing with a small amount of ether/benzene. After recrystallization from ether/benzene, valtratbromhydrin is obtained with a melting point of 66°–68° C.

EXAMPLE 8

Valtratiodohydrin 5 g of valtratum and 10 g of sodium acetate were dissolved in 50 ml of glacial acetic acid and the solution was reacted with a solution of 1.785 g of sodium iodide in 8 ml water. After 4 hours of standing at 0° to 5° C., the mixture, solidified to a crystalline slurry, was diluted with ice water, and the valtratiodohydrin was then filtered off, washed with water, and dried in vacuum at 60° C. The liquors were again extracted with ether, and the ether phase was dried, washed and evaporated, whereby valtratiodohydrin was again obtained as the residue. The combined valtratiodohydrin was recrystallized from ether/n-heptane. 5.58 g (corresponding to a yield of 86%) were obtained with a melting point of 112° C.

EXAMPLE 9

Didrovaltratbenzoyloxyhydrin 12.6 g of a 25% methanol solution of tetrabutylammoniumhydroxide were reacted with 3 g of benzoic acid. The solution was evaporated and the tetrabutylammonium benzoate remaining as the residue was dissolved in 12 ml of acetonitrile. To the solution, 2 g of didrovaltratum (containing approximately 15% homodidrovaltratum) were added and the reaction mixture agitated for 4 hours at 80° C. For processing, the cooled solution was evaporated in vacuum. The raw product remaining as the residue was purified over silica gel, using methylene chloride containing up to 6% ether as the eluting agent. From the different eluates, 500 mg of a slightly impure product and 2.08 g of a thin layer chromatographically-pure product were obtained as an oil. The initially oily didrovaltratbenzoyloxyhydrin (containing about 15% homodidrovaltratbenzoyloxyhydrin) crystallized while standing. After recrystallization from hexane/ether, the product had a melting point of 85° to 86° C.

Yield: 80.6%. $[a]_D^{20} = -22.9°$ (c=1 in $CH_3OH$)

EXAMPLE 10

Didrovaltrat(2-chlorphenyl)acetoxyhydrin 6.4 g of a 25% tetrabutylammonium hydroxide solution were reacted with 2.1 g of 2-chlorophenyl acetic acid, and the solution was evaporated in vacuum. The tetrabutylammonium-(2-chlorophenyl) acetate remaining in the residue was dissolved in 6 ml of acetonitrile, and the solution was then reacted with 1 g of didrovaltratum (containing about 20% homodidrovaltratum) and agitated for 2 to 3 hours at 80° C. For processing, the solution was evaporated in vacuum. The raw product remaining as the residue was purified chromatographically over a silica gel column using methylene chloride with up to 10% ether as the eluting agent.

From the eluate fractions, 700 mg of purified didrovaltrat(2-chlorphenyl)acetoxyhydrin (containing approximately 15% homocompound) were obtained as an oil.

$[a]_D^{20} = -24.4°$ (c=1 in $CH_3OH$)

EXAMPLE 11

Isovaleroyloxyhydroxydidrovaltratchlorohydrin (=IVHD-chlorhydrin)

22 g of raw isovaleroyloxyhydroxydidrovaltrate (containing admixtures of other valepotriates) were dissolved in 100 ml acetonitrile. The solution was reacted with 22 g of benzyltriethylammonium chloride and the reaction mixture agitated for 8 hours at 60° C. Subsequently, 0.5 ml of glacial acetic acid was added and the mixture agitated again for 2 hours at 60° C. For processing, the reaction mixture was diluted with ice water and extracted with ether. The organic phase was dried over sodium sulfate, filtered, and evaporated in vacuum to dryness. The raw product obtained as the residue was purified chromatographically over silica gel using 2-butanone containing n-hexane. 15.96 g of the raw product were obtained. This was dissolved in ether and extracted once with a sodium bicarbonate solution and once with water. Subsequently, the ether phase was dried over sodium sulfate and evaporated to dryness. After repeated recrystallization from n-hexane/ether, 1.14 g of isovaleroyloxyhydroxydidrovaltratchlorhydrin with a melting point of 80° C. were obtained.

$[a]_D^{20} = -55°$ (c=1 in $CH_3OH$)

EXAMPLE 12

Deacetyl-11-$\beta$-hydroxyisovaleroyloxyvaltratiodohydrin 8 g of a mixture of deacetyl-11-$\beta$-hydroxyisovaleroylvaltratum with isovaleroyloxyhydroxydidrovaltratum, didrovaltratum, homodidrovaltratum, and 1-$\alpha$-acevaltratum were dissolved with 16 g of sodium acetate in 100 ml of glacial acetic acid, and the solution was then reacted with 5 g of sodium iodide in 20 ml of water. The reaction mixture was agitated for 2 hours at room temperature, then diluted with 300 ml of water and extracted with ether. The organic phase was dried over sodium sulfate, filtered, and evaporated in vacuum. From the raw iodohydrin mixture, the above-mentioned compound was separated chromatographically.

To prepare the column needed for the chromatographic separation, 400 g of aluminum oxide were slurried in 500 ml of n-hexane and 40 ml of glacial acetic acid, poured into a column, and washed free of acid with n-hexane. The iodohydrin mixture to be separated was charged into this column and eluted with n-hexane containing increasing amounts of 2-butanone. By varying the 2-butanone addition in the eluting agent, individual iodohydrins were eluted from the mixture in fractions. Following the elution of the other iodohydrins with n-hexane which contained increasing amounts of up to 50% of n-butanone the deacetyl-11-β-hydroxyisovaleroylvaltratiodohydrin is eluted with 100% 2-butanone from the column. From the eluate, 0.71 g of deacetyl-11-β-hydroxyisovaleroylvaltratiodohydrin (containing 30% of the corresponding homocompounds) is obtained.

The following valepotriate hydrins were prepared in a manner similar to the above-described examples:

| | | | -continued |
|---|---|---|---|
| | | colloidal silica | 1 mg |
| | | magnesium stearate | 2 mg |
| | | | 200 mg |

The seived substances were intermixed and the powder thereby obtained poured into capsules in portions of 200 mg.

| Example No. | Name of Substance | $[\alpha]^{20}$ (c = 1, CH$_3$OH) | Note: (H: = Homocompound content according to the NMR spectrum) | |
|---|---|---|---|---|
| 13 | Didrovaltrat-(4-methylbenzoyl)oxyhydrin | −23.5° | H: 10% | Fp 76–78° C. |
| 14 | Didrovaltrat-(2-chlorbenzoyl)oxyhydrin | −23.2° | H: 20% | Fp 100–101° C. |
| 15 | Didrovaltrat-(3-trifluormethylbenzoyl)-oxyhydrin | −12.4° | H: 15% | |
| 16 | Didrovaltrat-(3-methoxybenzoyl)oxyhydrin | −11.6° | H: 15% | |
| 17 | Didrovaltrat-(3,4-dimethoxybenzoyl)-oxyhydrin | −8.5° | H: 15% | |
| 18 | Didrovaltrat-(3,4,5-trimethoxyphenyl)-acetoxyhydrin | −14.0° | H: 20% | |
| 19 | Didrovaltrat-(2-methoxyphenyl)acetoxyhydrin | −34.5° | H: 15% | Mp 93–94° C. |
| 20 | Didrovaltrat-(4-fluorphenyl)acetoxyhydrin | −23.0° | H: 15% | |
| 21 | Didrovaltratcinnamoyloxyhydrin | −31.7° | H: 20% | |
| 22 | Didrovaltratcaprinoyloxyhydrin | −28.6° | H: 10% | |
| 23 | Didrovaltratoleyloxyhydrin | −21.1° | H: 20% | |
| 24 | Didrovaltrat-(4-hydroxybenzoyl)oxyhydrin | −2.4° | H: 20% | |
| 25 | Didrovaltrat-(3,4-dihydroxybenzoyl)oxyhydrin | −13.9° | H: 20% | |
| 26 | Didrovaltrat-(2-hydroxybenzoyl)oxyhydrin | −9.3° | H: 15% | |

EXAMPLE I

Didrovaltratchlorohydrin-containing tablets

Tablets with the following composition per tablet were prepared:

Didrovaltratchlorohydrin (containing approximately 20% homodidrovaltratchlorohydrin): 25 mg
microcrystalline cellulose (Avicel ® PH 101): 78 mg
high dispersion silica (Aerosil ® R 972): 12.5 mg
carboxymethylcellulose (Tylose ®): 7 mg The active ingredient was dissolved in methylene chloride. The microcrystalline cellulose and the highly dispersed silica were mixed and ground together with the solution of the active ingredient. The resultant ground mixture obtained was dried and wetted with an aqueous tylose solution. The wet granulate obtained was pressed through a sieve with a 2 mm mesh, dried in a fluidized bed dryer at 40°–45° C., and again passed through a sieve with a mesh of 1.5 mm. The granulate was then mixed in a mixer with the following additional, auxiliary substances:

cross-linked polyvinylpyrrolidone (crospovidone USP 20/NF 15 3): 4.5 mg
magnesium stearate: 1.5 mg
high dispersion silica and was then pressed into 130 mg tablets.: 1.5 mg

EXAMPLE II

Didrovaltratbenzoyloxyhydrin-containing capsules

Capsules with the following composition were prepared:

| | |
|---|---|
| Didrovaltratbenzoyloxyhydrin | 10 mg |
| mannite | 175 mg |
| talcum | 12 mg |

EXAMPLE III

Didrovaltratisovaleroyloxyhydrin-containing soft gelatin capsules

| Composition | |
|---|---|
| didrovaltratisovaleroyloxyhydrin (containing about 20% homodidrovaltratisovaleroyloxyhydrin) | 30 p.b.w. |
| Migloyl 812 ® (oily triglyceride mixture of saturated vegetable fatty acids with chain lengths of C8, C10 and C12. Manufacturer: Dynamit Nobel AG.) | 278 p.b.w. |
| Total | 308 p.b.w. |

Preparation:

The active ingredient was dissolved with slight heating and agitation in Migloyl 812. The solution was processed into soft gelatin capsules containing, on the average, 302 μml of the solution. Valepotriate active ingredient per capsule: 30 mg.

EXAMPLE IV

Didrovaltrat-(2-chlorphenyl)acetohydrin-containing suppositories.

Suppositories of the following composition per suppository were prepared:

didrovaltrat-(2-chlorphenyl)acetohydrin (containing about 20% homodidrovaltrat-(2-chlorphenyl)acetohydrin): 20 mg
cocoa butter: 1980 mg The active ingredient and the finely ground suppository base mass were melted together and thoroughly mixed. From the melt, which was maintained in a homogeneous state by agitation, 2 g suppositories were molded.

EXAMPLE V

Isovaltratchlorohydrin containing capsules.
Capsules with the following composition are prepared:

| | |
|---|---|
| isovaltratchlorohydrin | 20 mg |
| mannite | 165 mg |
| talcum | 12 mg |
| colloidal silica | 1 mg |
| magnesium stearate | 2 mg |
| | 200 mg |

The screened substances were intermixed and the powder thereby obtained was poured into capsules in portions of 200 mg.

What is claimed is:

1. A method of treating or inhibiting disorders selected from the group consisting of motility disturbances and ulcers in the gastrointestinal tract of a mammal, comprising administering an effective gastrointestinal tract-normalizing or ulcer-inhibiting amount of an active compound having the formula:

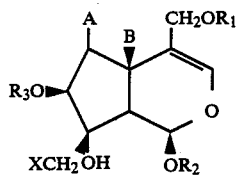

wherein
   A denotes a hydrogen
   B denotes a hydrogen or a hydroxy; or
   A and B together denote a bond; of $R_1$, $R_2$ and $R_3$,
      (i) one denotes an isovaleroyl group,
      (ii) another an acetyl group, and
      (iii) the other denotes an aceyl group of an acid selected from the group consisting of isovalerianic acid, β-methylvalerianic acid, α-isovaleroyloxyisovalerianic acid, α-acetoxyisovalerianic acid, β-acetoxyisovalerianic acid, β-acetoxy-β-methylvalerianic acid and β-hydroxyisovalerianic acid; and
   X denotes a halogen, a cyano, a rhodano, an azido or an acyloxy group having the formula $R_4COO$ wherein $R_4$ denotes
   (a) an unsubstituted or hydroxy-substituted alkyl group with 1 to 20 carbon atoms,
   (b) an alkenyl group with 3 to 20 carbon atoms, or
   (c) a constituent selected from the group consisting of a phenyl, a phenylalkyl with an alkylene chain containing up to 3 carbon atoms, and a phenylalkenyl group wherein the alkenylene chain contains up to carbon atoms, said constituent being ubsubstituted or substituted on the phenyl ring by a halogen, a trifluoromethyl, a hydroxy, lower alkyl, or a lower alkoxy.

2. A method according to claim 1, wherein X denotes a halogen, alkanoyloxy with 2 to 10 carbon atoms, or a constituent selected from the group consisting of a benzoyloxy, a phenylalkanoyloxy wherein the alkanoyloxy group contains up to 3 carbon atoms, and a phenylalkenoyloxy wherein the alkenoyloxy group contains up to 3 carbon atoms, said constituent being ubsubstituted or substituted on the phenyl ring by a halogen, a lower alkoxy, or a lower alkyl.

3. A method according to claim 1, wherein $R_2$ denotes isovaleroyl or β-methylvaleroyl.

4. A method according to claim 3, wherein $R_1$ and $R_3$ are different and
   (A) one of $R_1$ and $R_3$ denotes an acetyl and the other denotes isovaleroyl or β-acetoxyisovaleroyl, or
   (B) if B denotes a hydroxy, one of $R_1$ and $R_3$ denotes acetyl and the other denotes α-isovaleroyloxyisovaleroyl.

5. A method according to claim 1, wherein A and B each denotes a hydrogen.

6. A method according to claim 5, wherein $R_1$ denotes isovaleroyl, $R_2$ denotes isovaleroyl or β-methylvaleroyl, and $R_3$ denotes acetyl.

7. A method according to claim 6, wherein X denotes a halogen, an alkanoxyloxy with 2 to 10 carbon atoms, or a constituent selected from the group consisting of a benzoyloxy, a phenylalkanoyloxy wherein the alkanoyloxy group contains up to 3 carbon atoms, and a phenylalkenoyloxy wherein the alkenoyloxy group contains up to 3 carbon atoms, said constituent being unsubstituted or substituted on the phenyl ring by a halogen, a lower alkoxy, or a lower alkyl.

8. A method according to claim 1, which comprises administering at least one active compound selected from the group consisting of didrovaltratchlorhydrin and homodidrovaltratchlorhydrin.

9. A method according to claim 1, which comprises administering at least one active compound selected from the group consisting of a didrovaltratalkanoyloxyhydrin and a homodidrovaltratalkanoyloxyhydrin.

10. A method according to claim 9, wherein the alkanoyloxy group of said compound contains 2 to 7 carbon atoms.

11. A method according to claim 10, wherein said alkanoyloxy group is isovaleroyloxy.

12. A method according to claim 7, wherein X denotes a constituent selected from the group consisting of benzoyloxy and phenylacetoxy, said constituent being unsubstituted or substituted on a phenyl ring by chlorine.

13. A method according to claim 1, wherein A denotes hydrogen, B denotes hydroxy, X denotes a halogen, $R_2$ denotes isovaleroyl or β-methylvaleroyl, and one of $R_1$ and $R_3$ denotes acetyl and the other denotes isovaleroyl, β-acetoxyisovaleroyl, or α-isovaleroyloxyisovaleroyl.

14. A method according to claim 1, wherein A and B together denote a bond.

15. A method according to claim 14, wherein one of $R_1$ and $R_3$ denotes acetyl and the other denotes isovaleroyl or β-acetoxyisovaleroyl, and $R_2$ denotes isovaleroyl or β-methylvaleroyl.

* * * * *